US010683495B2

(12) United States Patent
Bunk et al.

(10) Patent No.: US 10,683,495 B2
(45) Date of Patent: Jun. 16, 2020

(54) METHOD FOR PREPARING ELECTROCOMPETENT YEAST CELLS, AND METHOD FOR USING SAID CELLS

(71) Applicant: immatics biotechnologies GmbH, Tuebingen (DE)

(72) Inventors: Sebastian Bunk, Tuebingen (DE); Dominik Maurer, Moessingen (DE); Felix Unverdorben, Stuttgart (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 130 days.

(21) Appl. No.: 15/813,879

(22) Filed: Nov. 15, 2017

(65) Prior Publication Data
US 2018/0135039 A1 May 17, 2018

(30) Foreign Application Priority Data
Nov. 15, 2016 (DE) .................. 10 2016 121 899

(51) Int. Cl.
C12N 13/00 (2006.01)
C12N 15/90 (2006.01)
C12N 1/16 (2006.01)
C12N 15/87 (2006.01)
C07K 14/725 (2006.01)
C12N 15/10 (2006.01)

(52) U.S. Cl.
CPC .......... C12N 13/00 (2013.01); C07K 14/7051 (2013.01); C12N 1/16 (2013.01); C12N 15/1037 (2013.01); C12N 15/87 (2013.01); C12N 15/905 (2013.01)

(58) Field of Classification Search
CPC ...... C07K 14/7051; C12N 1/16; C12N 13/00; C12N 15/1037; C12N 15/87; C12N 15/905
See application file for complete search history.

(56) References Cited

U.S. PATENT DOCUMENTS

2009/0264320 A1* 10/2009 Hsieh ............... C12N 13/00
506/26

FOREIGN PATENT DOCUMENTS

| WO | 2009/114093 A2 | 9/2009 |
| WO | 2009114096 A2 | 9/2009 |
| WO | 2016/102508 A1 | 6/2016 |
| WO | 2016102508 A1 | 6/2016 |

OTHER PUBLICATIONS

Benatuil et al. (Protein Engineering, Design & Selection, 2010,vol. 23 No. 4 pp. 155-159) (Year: 2010).*
Cline et al. (Biochemistry, 2004, 43:15195-15203) (Year: 2004).*
Suga et al. (Curr. Gen., 2003, 43:206-211) (Year: 2003).*
Holler et al. (Proc. Natl. Acad. Sci., 2000, 97(10):5387-5392) (Year: 2000).*

(Continued)

Primary Examiner — Jeremy C Flinders
(74) Attorney, Agent, or Firm — McBee Moore & Vanik IP, LLC

(57) ABSTRACT

The present invention relates to improved yeast transformation of yeast cells and yeast cell libraries transformed thereby. More specifically, the present invention relates to the transformation of yeast by electroporation.

19 Claims, 1 Drawing Sheet

(56) References Cited

OTHER PUBLICATIONS

International Search Report for PCT/EP2017/079011, dated Jan. 25, 2018.
Search report for German Application No. 102016121899.5, dated Jul. 4, 2017.
Wen, F.: Cell surface display in biomedical applications and biofuels production. Thesis, University of Illinois at Urbana-Champaign, 2010, S. 44-45.
Smith et al., "T Cell Receptor Engineering and Analysis Using the Yeast Display Platform" Methods Mol. Biol. (2015) 1319: 95-141.

* cited by examiner

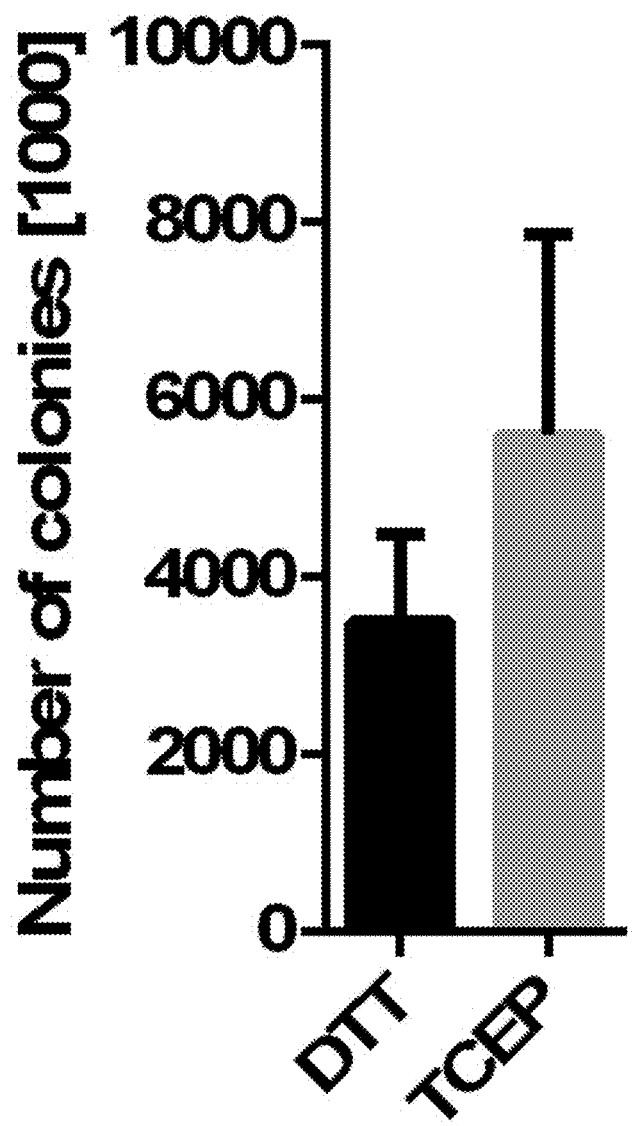

METHOD FOR PREPARING ELECTROCOMPETENT YEAST CELLS, AND METHOD FOR USING SAID CELLS

CROSS REFERENCE TO RELATED APPLICATIONS

This application claims the benefit to German Application No. 102016121899.5, filed 15 Nov. 2016, the content of the application is herein incorporated by reference in their entirety.

This application also is related to PCT/EP2017/079011 filed 13 Nov. 2017 the content of which is incorporated herein by reference in its entirety.

FIELD

The present invention relates to improved yeast transformation of yeast cells and yeast cell libraries transformed thereby. More specifically, the present invention relates to the transformation of yeast by electroporation.

BACKGROUND

For years, the cornerstones of cancer treatment have been surgery, chemotherapy, and radiation therapy. Over the last decade, targeted therapies like imatinib (Gleevec®) and trastuzumab (Herceptin®)—drugs that target cancer cells by homing in on specific molecular changes seen primarily in those cells—have also emerged as standard treatments for a number of cancers.

Now, excitement is growing for immunotherapy-therapies that harness the power of a patient's immune system to combat their disease. One approach to immunotherapy involves engineering patients' own immune cells to recognize and attack their tumors. This approach, called adoptive cell transfer (ACT), has generated some remarkable responses in patients with advanced cancer.

While it is typically expected that natural T-cell receptors (TCRs) are of sufficiently high affinity to achieve therapeutic efficacy, when developing therapeutic TCRs or derivatives thereof, such as, for example, soluble TCRs (sTCRs), usually a so-called affinity maturation is desired/required to elicit a productive immune response in vivo.

For the maturation, a method using yeast surface display technology is commonly employed. Nevertheless, in order to generate libraries that have a sufficient diversity, a highly efficient method for yeast transformation is necessary.

It has long been desirable to identify TCRs consisting essentially of natural alpha and beta chain sequences that specifically bind to particular antigens, such that for example the TCRs, or their soluble analogues, can be developed to provide basis for potential therapeutics. The antigens recognized by the identified TCRs may be associated with a disease, such as cancer, viral infections, autoimmune diseases, parasitic infections and bacterial infections. Therefore, such therapies can be used for the treatment of said diseases.

Furthermore, once natural or native TCRs have been identified and their sequences determined, mutations can be introduced that result in an increase in affinity or half-life, as needed, such as described in WO2012/013913. Traditionally, attempts to identify TCRs that specifically bind to disease-associated antigens, such as cancer viral, autoimmune or bacterial antigens, have been limited to the use of blood samples taken from volunteer donors. Such samples are used to isolate T cells and their corresponding TCRs which bind disease associated antigens. This approach generally requires at least 20 donors. The process is long and labor intensive, and there is no guarantee of identifying antigen binding T cell receptors. Where functional T cell receptors are identified they often have weak affinity for antigen, low specificity, and/or do not fold properly in vitro. The diversity of T cells that are able to be screened is limited to the T cell diversity within donors. Some disease-associated antigens, including the majority of cancer-antigens, are self-antigens; since thymic selection serves to remove TCRs that recognize self-antigens, TCRs specific for disease associated antigens may not be present in the natural repertoire of the donors, or else may have weak affinity for antigen.

Attempts to design a library for the isolation of new TCRs with antigen binding specificity have been on-going for several years. TCRs libraries are far more difficult to create than comparable antibody libraries, since TCR chains are less stable and often do not display correctly. The complexities involved in constructing a library of TCRs are enormous. Retaining variation in CDR3 length, (as found in natural repertoires) is preferable. A substantial portion of any library is generally lost to stop codons, frame shifts, folding problems and TCR chain combinations that could simply never bind to an HLA complex. Taking into account the large number of variable alpha and variable beta genes, as well as the J and D genes, the chance of producing and identifying a functional folding alpha chain and a functional folding beta chain that together form a TCR that binds to an antigenic peptide with the required specificity is extremely low. The availability of means for the production of nucleic acid libraries and recombinant products produced thereby, such as pharmaceutical proteins, in eukaryotic systems such as yeast, provides significant advantages relative to the use of prokaryotic systems such as E. coli. Yeast can generally be grown to higher cell densities than bacteria and are readily adaptable to continuous fermentation processing. However, the development of yeast species as host/vector systems for the production of recombinant products and libraries is severely hampered by the lack of knowledge about transformation conditions and suitable means for stably introducing foreign nucleic acids into the yeast host cell.

Among the various electrical and biological parameters that facilitate electrotransformation of cells is the adsorption of DNA to the cell surface. Alternating electric fields of low intensity also promote DNA transfer into E. coli bacteria, presumably by the electrical stimulation of DNA permeases. Evidence for the dominant electrodiffusive or electrophoretic effect on electroporative gene transfer of polyelectrolyte DNA has accumulated. Electroosmotic effects and membrane invagination facilitated by electroporation have also been reported.

The application of an electrical field across a yeast cell membrane results in the creation of transient pores that are critical to the electroporation process. An electroporator signal generator provides the voltage (in kV) that travels across the gap (in cm) between the electrodes. This potential difference defines what is called the electric field strength where E equals kV/cm. Each cell has its own critical field strength for optimum electroporation. This is due to cell size, membrane make-up and individual characteristics of the cell wall itself. For example, mammalian cells typically require between 0.5 and 5.0 kV/cm before cell death and/or electroporation occurs. Generally, the required field strength varies inversely with the size of the cell.

EP2257638A1 relates to methods for the transformation of yeast by electroporation. These include the combination of lithium acetate (LiAc) and dithiothreitol (DTT) as cell conditioning agents, both of which have been used to enhance the frequency of yeast transformation. As shown in Table 2, the elimination of DTT or LiAc pre-treatment resulted in respective efficiency reductions of 93.3% and 85.7%.

Similarly, Smith et al. (in: T Cell Receptor Engineering and Analysis Using the Yeast Display Platform. Methods Mol Biol. 2015; 1319:95-141) disclose a study regarding the TCR in the binding of antigens as peptide-MHC (pepMHC) ligands. There has been interest in engineering the affinity of TCRs in order to use this class of molecules in ways similar to now done with antibodies. To engineer TCRs, and to analyze their binding features more rapidly, they have used a yeast display system as a platform. Expression and engineering of a single-chain form of the TCR, analogous to scFv fragments from antibodies, allow the TCR to be affinity matured with a variety of possible pepMHC ligands. In addition, the yeast display platform allows one to rapidly generate TCR variants with diverse binding affinities and to analyze specificity and affinity without the need for purification of soluble forms of the TCRs. The article describes the methods for engineering and analyzing single-chain TCRs using yeast display.

Yeast libraries have not achieved the size or efficiency that has been achieved by phage libraries, a typical maximal phage library size for is $10^{10}$ to $10^{11}$, whereas a typical yeast library is $10^7$ in size. Although recent progress in electroporation protocols (see Chao, Nature Protocols 1(2):755-768 (2006)) has made it possible to achieve a maximal $5 \times 10^7$ yeast library size in a single transformation. It is still a correct statement that yeast library sizes achieved to date are still significantly below what is routinely achievable by phage display libraries in the $10^{10}$ to $10^{11}$ size.

The above methods and disclosures while achieving increasingly higher transformation efficiency are still laborious and take significant time and repetitive efforts to accumulate multiple small libraries in the $10^6$ to $10^7$ size ranges to a larger and combined library size in the $10^8$ to $10^9$ size range.

Yeast display library selection, using both magnetic bead and fluorescence-activated cell sorting, offers an efficient and sensitive method to enrich specific binders to target antigens, in particular by its compatibility with fluorescence activated cell sorting (FACS). The advantage of this selection power, however, is hampered by the limited size of typical yeast display libraries due to the low transformation efficiency of yeast cells.

A need therefore exists for efficient methods for producing protein libraries, e.g., TCR libraries, using yeast.

In one aspect of the present invention, a method for preparing electrocompetent yeast cells is provided, comprising the steps of: a) growing yeast cells to an $OD_{600}$ of between about 1.0 to 2; b) washing the cells with cold water; c) washing the cells with a cold solution comprising sorbitol and $CaCl_2$; d) incubating the cells a solution comprising lithium acetate and tris2-carboxyethyl)phosphine (TCEP); e) washing the cells with a cold solution comprising sorbitol and $CaCl_2$; f) resuspending the cells in a solution comprising sorbitol; and g) optionally, suitably storing said cells.

The invention thereby provides a highly efficient method of transforming yeast cells, for example for the production of improved yeast cell libraries. The methods of the invention remove a significant bottleneck in applying yeast display technology as a practical tool to access a much larger TCR diversity space previously unexplored.

Yet another aspect of the present invention then relates to a method for transfecting electrocompetent yeast cells, comprising the steps of: a) providing electrocompetent yeast cells according to the method according to the present invention; b) washing the cells with a cold solution comprising sorbitol; c) mixing the cells with the DNA to be transfected, to form a preelectroporation-mix; d) transferring said pre-electroporation-mix into a suitable electroporation cuvette, and e) electroporating said cells at between about 2.5 kV/cm to about 12.5 kV/cm for between about 2 to about 5 ms.

Preferred is a method according to the present invention, wherein said DNA is linear or circular. More preferred is a method according to the present invention, wherein said DNA comprises a library of DNA fragments encoding for a library of proteins of interest, for example in the form of a yeast surface display library. Most preferred is a method according to the present invention, wherein said display library is a T-cell receptor (TCR) library.

It was surprisingly found that by using tris2-carboxyethyl) phosphine (TCEP) as a reducing agent, the transformation efficiency of the method according to the present invention is higher compared to DTT, for example higher than $1 \times 10^8$ yeast transformants/μg vector DNA, preferably higher than $2 \times 10^8$ yeast transformants/μg vector DNA.

Yet another aspect of the present invention then relates to a method for producing an improved yeast library of proteins of interest, for example in the form of a yeast surface display library, comprising the steps of: a) providing a transfected yeast cells according to the method according to the present invention; b) diluting the transfected cells into a 1:1 mix of a solution of sorbitol in growth medium; c) resuspending cells in suitable growth medium; d) optionally, performing dilutions for a calculation of diversity, and plating said dilutions on SD-CAA plates containing kanamycin; and e) transferring said library into suitable growth medium and expanding said library per electroporation; and f) optionally, suitably storing said expanded library.

Preferred is a method according to the present invention, wherein said display library is a T-cell receptor library. Preferred is a method according to the present invention, wherein the diversity of said library is higher than about $10^{12}$.

In the context of the present invention, the term "expression vector" means a DNA construct that includes an autonomous site of replication (ARS), a site of transcription initiation and at least one structural gene coding for a protein that is to be expressed in the host organism. A site of replication, or origin of replication, is any DNA sequence that controls the replication of the cloning and expression vectors. An expression vector usually also contains appropriate control regions such as one or more enhancers and/or promoters, suppressors and/or silencers, and terminators that control the expression of the protein in the host yeast. Expression vectors according to the present invention may also contain a selection marker comprising an essential gene as described herein. The expression vector also optionally contains other selectable markers widely available and well known to those of skill in the art. Expression vectors are one type of vector. Vectors may optionally include one or more ARS sequences (elements) from one or more strains of yeast.

The term "operably linked" means that DNA segments are arranged so that they function in concert for their intended purposes, e.g., transcription initiates in the promoter and proceeds through the coding segment to the terminator.

The term "transformation" or "transfection" means the introduction of DNA or other nucleic acids into a recipient yeast host cell that changes the genotype.

The term "transformant," or a "transformed cell," means a recipient yeast host cell, and progeny thereof, that has undergone transformation.

"About" shall mean+/−10% of the given value, unless noted otherwise.

Vectors useful in the electroporation methods of the invention include the pYD vector any other vectors and their derivative constructs that can be propagated by yeast cells, or nucleic acids in general. The expression vector of the present invention may be based on any type of vector as long as the vector can transform, transfect or transduce a host yeast cell. In a preferred embodiment, the expression vector is based on a yeast plasmid, especially one from *S. cerevisiae*. After transformation of yeast cells, the exogenous DNA encoding the library sequences is taken up by the cells and subsequently expressed by the transformed cells.

More preferably, the expression vector may be a yeast-bacteria shuttle vector that can be propagated in either *E. coli* or yeast (Struhl, et al. (1979) Proc. Natl. Acad. Sci.). The inclusion of *E. coli* plasmid DNA sequences, such as pBR322, facilitates the quantitative preparation of vector DNA in *E. coli*, and thus the efficient transformation of yeast.

The types of yeast plasmid vectors that may serve as the shuttle may be a replicating vector or an integrating vector. A replicating vector is a yeast vector that is capable of mediating its own maintenance, independent of the chromosomal DNA of yeast, by virtue of the presence of a functional origin of DNA replication. An integrating vector relies upon recombination with the chromosomal DNA to facilitate replication and thus the continued maintenance of the recombinant DNA in the host cell. A replicating vector may be a 2 micron-based plasmid vector in which the origin of DNA replication is derived from the endogenous 2 micron plasmid yeast. Alternatively, the replicating vector may be an autonomously replicating (ARS) vector, in which the "apparent" origin of replication is derived from the chromosomal DNA of yeast. Optionally, the replicating vector may be a centromeric (CEN) plasmid that carries in addition to one of the above origins of DNA replication a sequence of yeast chromosomal DNA known to harbor a centromere.

The vectors may be transformed into yeast cells in closed circular form or in a linear form. Transformation of yeast by integrating vectors, although with heritable stability, may not be efficient when the vector is in a close circular form (e.g., yielding only about 1-10 transformants per μg of DNA). Linearized vectors, with free ends located in DNA sequences homologous with yeast chromosomal DNA, transform yeast with higher efficiency (100-1000 fold) and the transforming DNA is generally found integrated into sequences homologous to the site of cleavage. Thus, by cleaving the vector DNA with a suitable restriction endonuclease, it is possible to increase the efficiency of transformation and target the site of chromosomal integration. Integrative transformation may be applicable to the genetic modification of brewing yeast, providing that the efficiency of transformation is sufficiently high and the target DNA sequence for integration is within a region that does not disrupt genes essential to the metabolism of the host cell.

Yeast strains that can be transformed by the electroporation method of the invention include yeast species in the *Saccharomyces* genus such as *Saccharomyces cerevisiae* and the *Schizosaccharomyces* genus such as *Schizosaccharomyces Pombe*. In one embodiment, the yeast cells are diploid yeast cells. Alternatively, the yeast cells are haploid cells such as the "a" and "a" strain of yeast haploid cells.

A "T-cell receptor library" in the context of the present invention may comprise suitable parts of human and/or mutated human TCRs to be screened, preferably a single-chain form of the TCR, e.g. a $V_\beta$-linker-$V_\alpha$ single chain (scTCR); or a $V_\alpha$-linker-$V_\beta$ single chain, optionally fused to a self-cleaving peptide, e.g. 2A-peptide. Published methods to optimize TCR expression with minimal modification to the wild type amino acid sequence can also be used (e.g. Szymczak, A. L. et al. Correction of multi-gene deficiency in vivo using a single 'self-cleaving' 2A peptide-based retroviral vector. Nat Biotechnol 22, 589-594 (2004); Yang, S. et al. Development of optimal bicistronic lentiviral vectors facilitates high-level TCR gene expression and robust tumor cell recognition. Gene Ther 15, 1411-1423 (2008); Kuball, J. et al. Facilitating matched pairing and expression of TCR chains introduced into human T cells. Blood 109, 2331-2338 (2007); Cohen, C. J. et al. Enhanced Antitumor Activity of T Cells Engineered to Express TCell Receptors with a Second Disulfide Bond. Cancer Res 67, 3898-3903 (2007); Scholten, K. B. J. et al. Codon modification of T cell receptors allows enhanced functional expression in transgenic human T cells. Clin. Immunol. 119, 135-145 (2006)).

The ratio of vector DNA to insert DNA is in the range of about 1:0.5 to about 1:10, for example, 1:0.5, 1:1; 1:2, 1:3, 1:4, 1:5, 1:6, 1:7, 1:8, 1:9, or 1:10. In an embodiment, about 1 μg of vector DNA and about 1 μg of insert DNA are used in a reaction. In another embodiment, about 1 μg of vector DNA and about 2 μg of insert DNA are precipitated. In another embodiment, about 1 μg of vector DNA and about 3 μg of insert DNA are precipitated. In still another embodiment, about 1 μg of vector DNA and about 4 μg of insert DNA are precipitated. In yet another embodiment, about 1 μg of vector DNA and about 5 μg of insert DNA are precipitated.

In an embodiment, the cell suspension comprises about 50 to about 400 μl of yeast cells, for example, 50, 100, 150, 200, 250, 300, 350, 400 μl of yeast cells.

In an embodiment, the yeast cells suspension is about 1 to about $10\times10^9$ yeast cells/mL, for example, 1, 2, 3, 4, 5, 6, 7, 8, 9, or $10\times10^9$ yeast cells/mL.

In an embodiment, the field strength used to electroporate the yeast cells was about 0.5 kV/cm to about 12.5 kV/cm, for example, 0.5, 1.0, about 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, kV/cm.

In an embodiment, the yeast cells are electroporated at a capacitance of about 10 to about 50 μF, for example, 10, 15, 20, 25, 30, 35, 40, 45, or 50.

In an embodiment, the yeast cells are suspended in about 0.1 to about 10 M sorbitol and 0.1 to 10 mM $CaCl_2$ or $MgCl_2$, for example, 0.1, 0.25, 0.5, 0.75, 1.0, 2.0, 3.0, 4.0, 5.0, 6.0, 7.0, 8.0, 9.0, or 10.0 M sorbitol, or, for example, 0.1, 0.25, 0.5, 0.75, 1.0, 2.0, 3.0, 4.0, 5.0, 6.0, 7.0, 8.0, 9.0, or 10.0 mM $CaCl_2$ or $MgCl_2$ In an embodiment, the yeast cells are incubated in about 0.01 to about 1.0 M LiAc, for example, 0.01, 0.02, 0.03, 0.04, 0.05, 0.06, 0.07, 0.08, 0.09, 0.1, 0.2, 0.3, 0.4, 0.5, 0.6, about 0.7, 0.8, 0.9, or 1.0 M LiAc, and 1 to 100 mM TCEP, for example, 1, 10, 20, 30, 40, 50, 60, about 70, 80, 90, or 100 mM TCEP.

The invention provides methods for the transformation of yeast cells comprising electroporating a cell suspension containing yeast together with one or more nucleic acid constructs. The transformation of yeast cells can result in anywhere from a single clone to population of yeast cells (i.e., yeast library or libraries) that can be used to screen for (a) peptide(s) or protein(s) displayed on the surface of yeast cells by means of tethering to a yeast surface protein or association via a specific covalent bond or non-covalent interaction with yeast cell surface proteins or other components; (b) peptide(s) or protein(s) expressed intracellularly; or (c) peptide(s) or protein(s) that are secreted into extracellular space such as culture media, or deposited onto solid surface. Such yeast libraries can be conveniently amenable to multiple applications, to screen or characterize interactions between the peptide(s) or protein(s) to another protein, peptide, DNA, RNA or other chemical matters that can be introduced into the yeast cells or exogenously added. Specific examples are those found in yeast display, yeast two hybrid, yeast three hybrid, etc.

The invention provides a method for the transformation of yeast cells comprising electroporating a cell suspension containing yeast together with one or more nucleic acid constructs comprising one or more regulatory sequences and one or more genes or gene segments, using one or more of resistance, field strength and pulse duration sufficient to transform the yeast cells.

In an embodiment, field strength is from about 2.5 kV/cm to about 12.5 kV/cm. In certain embodiments, the field strength is 0.5 kV/cm, 1.0 kV/cm, 1.5 kV/cm, 2.0 kV/cm, or 2.5 kV/cm. These values take into account that the electroporation cuvette has a 0.2 cm gap. Higher field strengths are possible but their practicality is largely dependent upon the development of an apparatus that can deliver a stronger pulse.

In an embodiment, the pulse duration is from about 3 milliseconds to about 10 milliseconds. In a particular embodiment, the pulse duration is about 4 milliseconds.

Treatment of cells by the electroporation methods of the invention is carried out by applying an electric field to a yeast cell suspension between a pair of electrodes. The field strength must be adjusted reasonably accurately so that electroporation of the cells occurs without damage, or at with minimal damage, to the cells. The distance between the electrodes can then be measured and a suitable voltage according to the formula $E=V/d$ can then be applied to the electrodes ($E$=electric field strength in V/cm; $V$=voltage in volts; and $d$=distance in cm).

Pulse generators for carrying out the procedures described herein are and have been available on the market for a number of years. One suitable signal generator is the Gene Pulser II (BioRad Laboratories, Inc., Hercules, Calif.). A typical set up consists of the Gene Pulser II connected to a capacitance expender plus and the pulse controller plus modules.

Electroporation is used within the present invention to facilitate the introduction of DNA into yeast cells. Electroporation is the process of using a pulsed electric field to transiently permeabilize cell membranes, allowing macromolecules, such as DNA, to pass into cells. However, the actual mechanism by which DNA is transferred into the cells is not well understood. For transformation of *Candida famata*, for example, electroporation is surprisingly efficient when the cells are exposed to an experimentally decaying pulsed electric field having a field strength of from about 10 to about 13 kV/cm and a resistance value of about R5 (129 ohms), and a time constant of about 4.5 ms. Typically, resistance and capacitance are either present or may be selected by the user, depending on the electroporation equipment selected. In any event, the equipment is configured in accordance with the manufacturer's instructions to provide field strength and decay parameters as appropriate.

The invention further relates to highly efficient methods of transformation of yeasts that allow for a high level of expression of any one or more desired endogenous (i.e., naturally existing within that yeast cell) or heterologous genes. The methods of the invention further relate to a method for preparing libraries, for example, that express TCRs, scTCRs, chimeras or fragments thereof.

In one scenario, expression vectors carrying genes of interest can be transformed into yeast host cells by electroporation to generate a single clone or a library comprised of many transformed cells expressing intracellular proteins (e.g., nuclear or cytoplasmic proteins), membrane proteins (e.g., membrane-spanning proteins or membrane attached proteins), or secreted proteins. One will be able to use the transformed cells or library to purify proteins, study protein functions, identify protein-protein interactions, or to identify novel protein binders or interaction partners. Of important note is the ability to generate very large yeast libraries displaying or expressing TCRs and TCR fragments. The library can be subjected to selection by target antigens to identify TCRs that bind to the selecting antigens.

As transformed yeast have a tendency to lose artificially-constructed plasmids, it is advantageous to use a culture medium so as to exert a positive selection pressure on them. When the strain is an auxotrophic mutant for an essential metabolite and when the vector plasmid used comprises a marker gene capable of restoring the strain prototrophy, for example, the LEU2 gene, this selection pressure may be exerted by omitting the metabolite from the culture medium. Other means exist to obtain the same result and may also be used to practice the invention.

Depending upon the nature of the structural gene of interest, the product or expression product may remain in the cytoplasm of the yeast host cell or be secreted. It has been found that not only the proteins that remain in the cell but also those that are secreted are soluble. Where the product or expression product is to remain in the yeast host cell, it may generally be desirable to have an inducible transcription initiation region, so that until the transformant has reached a high density, there is little or no expression or production of the desired product. After sufficient time for the product or expression product to be expressed, the cells may be isolated by conventional means, e.g., centrifugation, lysis and the product of interest isolated. Depending upon the nature and use of the product, the lysate may be subjected to various purification methods, such as chromatography, electrophoresis, solvent extraction, crystallization, dialysis, ultrafiltration or the like. Methods of chromatography include, but are not limited to, gas chromatography, HPLC, column chromatography, ion exchange chromatography and other methods of chromatography known to those of skill in the art. The degree of purity may vary from about 50%, to 90% or higher, preferably up to about 100%.

Alternatively, the expression product or product of interest may be secreted into the culture medium, and produced on a continuous basis, where the medium is partially withdrawn, the desired product extracted, e.g., by column or affinity chromatography, ultrafiltration, precipitation or the like, and the spent medium discarded or recirculated by restoring essential components. The permeate containing the product from the ultrafiltration can be further subjected to concentration, further by evaporation, followed by crystallization or precipitation using alcohol and/or pH adjustment. Those of skill in the art are aware of the many process options. When the product is to be secreted, normally a constitutive transcriptional initiation region will be employed, although nonconstitutive regions may be used.

Other preferred embodiments can be derived from the examples with reference to the figures as described herein, nevertheless, without being limited thereto. For the purposes of the invention, all references as cited herein are incorporated by reference in their entireties.

FIG. 1 shows a comparison of the improved transfection efficiency of TCEP, when compared with DTT under the same conditions.

EXAMPLES

The practice of the invention employs, unless otherwise indicated, conventional techniques of cellular electroporation and yeast cell biology, which are well known in the art.

I. Media

| 1. YPD media | |
| --- | --- |
| Yeast extract | 10 g |
| Bacto-peptone | 20 g |
| Dextrose | 20 g |
| bring volume to 1 L with H$_2$O (ad sterile glucose to autoclaved solution) | |
| 2. SD-CAA (pH 4.5): | |
| Sodium citrate dihydrate | 14.8 g (50 mM final) |
| Citric acid monohydrate | 4.2 g (20 mM final) |
| in 800 mL of H$_2$O, autoclave. | |
| Casamino acids | 5.0 g |
| Yeast nitrogen base (without amino acids) | 6.7 g |
| Glucose | 20 g |
| bring volume to 1 L with H$_2$O and sterile filter | |
| 3. SD-CAA plates: | |
| Sorbitol | 182.2 g |
| Agar | 15 g |
| Sodium citrate | 14.8 g |
| Citric acid monohydrate | 4.2 g |
| in 800 mL of H$_2$O, autoclave, and cool to ~55° C. | |
| Casamino acids | 5.0 g |
| Yeast nitrogen base (without amino acids) | 6.7 g |
| Glucose | 20 g |
| Kanamycin sulfate | 35 mg |
| in 200 ml H$_2$O and sterile filter, add to cooled autoclaved solution | |

II. Preparation of Electrocompetent Yeast Cells

20 µl of freshly thawed yeast stock from −80° C. were streaked out on YPD agar plates, and incubated for two days at 30 C. Single colonies (take whole colony) were taken from the YPD agar plate into 15 ml YPD media, and shaking was performed over night at 30° C. Next morning, 10 ml of culture were transferred into 100 ml fresh YPD medium, and shaking was continued for 7 h at 30 C. The OD$_{600}$ was determined and 1 l cold YPD medium was inoculated to an OD$_{600}$ of 0.2. The shaker flask was placed in a precooled (4° C.) shaker. The shaker was programmed to start heating (30° C.) and shaking (250 rpm) 5 h before work day begins. Incubation was performed until OD$_{600}$ reached 1.5 which was usually 6 h after shaking started.

Subsequent steps have to be performed on ice and with cooled solutions, tubes, cuvettes and centrifuge, if not stated otherwise.

The cells were pelleted at 2,000 g and 4° C. for 3 min (2 step process in 10 Falcon tubes, 50 ml), washed twice with 25 ml cold H$_2$O and pelleted at 2,000 g for 3 min. The cells were washed with 25 ml of cold sorbitol, 1 M/CaCl$_2$, 1 mM; and pelleted at 2,000 g for 3 min. The cells were resuspended in 25 ml lithium acetate, 100 mM/TCEP, 10 mM. A 50 ml Falcon tubes with filter lid was used to allow for aeration; the cells were incubated at 30° C. while shaking at 160 rpm for 30 min, placed on ice and the cells were pelleted at 2,000 g and 4° C. for 3 min. The cells were washed with 25 ml of cold 1 M sorbitol/1 mM CaCl$_2$; and pelleted at 2,000 g and 4° C. for 3 min, and washed with 25 ml of cold 1 M sorbitol; and pelleted at 2,000 g and 4° C. for 3 min. The cells were suspended in a conical tube in cold 1 M sorbitol to a final volume of 400 µl per electroporation reaction. Electrocompetent cells can be stored directly at −80° C. Before using the samples for electroporation, leaked salts have be removed by centrifugation (2,000 g, 4° C., 5 min) and washing twice with cold sorbitol, 1 M.

III. Electroporation

400 µl of cells were mixed with 5-10 µl DNA (vector) in H$_2$O, kept on ice for 3 min and transferred to a precooled 0.2 cm electroporation cuvette. Using a BioRad MicroPulser Electroporation System, the cells were electroporated at 2.5 kV. Typical time constants were at about 4 ms, preferably at 4 ms. The electroporated cells were transferred into 10 ml of 1:1 mix of 1 M sorbitol:YPD media at 30° C. for 1 hour without shaking. The cells were harvested at 2,000 g for 3 min at room temperature, and resuspended in 10 ml SD-CAA at room temperature. Dilutions were performed for calculation of diversity (1:10$^5$ to 1:10$^7$). Dilutions on SD-CAA plates containing kanamycin were incubated for 1 day at 30° C. and for three days at room temperature. The library was transferred into 100 ml SD-CAA (preferably per electroporation) and shaking was continued for 24 h at 30° C. at 160 rpm. Expanded libraries can be used directly for induction or stored at 4° C. for two weeks. Long term storage can be performed by freezing in 30% glycerol at −80° C.

By using the most optimal electroporation condition, one can routinely achieve yeast transformation efficiency of about 2×10$^8$ yeast transformants/µg vector DNA (see FIG. 1). As this transformation efficiency is achieved in minimal cell volume (100 µl), it is highly amenable to automation and multiwell electroporation devices.

The invention claimed is:

1. A method for preparing electrocompetent yeast cells comprising the steps of:
   a) growing yeast cells to an OD$_{600}$ of between 1.0 to 2;
   b) washing the cells with cold water;
   c) washing the cells with a cold solution comprising sorbitol and CaCl$_2$);
   d) incubating the cells a solution comprising lithium acetate and tris2-carboxyethyl)phosphine (TCEP);
   e) washing the cells with a cold solution comprising sorbitol and CaCl$_2$);
   f) resuspending the cells in a solution comprising sorbitol; and
   g) optionally, suitably storing said cells.

2. A method for transfecting electrocompetent yeast cells, comprising the steps of:
   a) providing electrocompetent yeast cells according to the method according to claim 1;
   b) washing the cells with a cold solution comprising sorbitol;
   c) mixing the cells with the DNA to be transfected, to form a pre-electroporation-mix;
   d) transferring said pre-electroporation-mix into a suitable electroporation cuvette, and
   e) electroporating said cells at between 2.5 kV/cm to 12.5 kV/cm for between 2 to 5 ms.

3. The method according to claim 2, wherein said DNA is linear or circular.

4. The method according to claim 2, wherein said DNA comprises a library of DNA fragments encoding for a library of proteins of interest in the form of a yeast surface display library.

5. The method according to claim 4, wherein said display library is a T-cell receptor (TCR) library.

6. The method according to claim 2, wherein the transformation efficiency is higher than $1\times10^8$ yeast transformants/µg vector DNA.

7. A method for producing an improved yeast library of proteins of interest, for example in the form of a yeast surface display library, comprising the steps of:
 a) providing a transfected yeast cells according to the method according to claim 2;
 b) diluting the transfected cells into a 1:1 mix of a solution of sorbitol in growth medium;
 c) resuspending cells in suitable growth medium;
 d) optionally, performing dilutions for a calculation of diversity, and plating said dilutions on SD-CAA plates containing kanamycin; and
 e) transferring said library into suitable growth medium and expanding said library per electroporation; and
 f) optionally, suitably storing said expanded library.

8. The method according to claim 7, wherein said display library is a T-cell receptor library.

9. The method according to claim 7, wherein the diversity of said library is higher than $10^{12}$.

10. The method according to claim 3, wherein said DNA comprises a library of DNA fragments encoding for a library of proteins of interest in the form of a yeast surface display library.

11. The method according to claim 3, wherein the transformation efficiency is higher than about $2\times10^8$ yeast transformants/µg vector DNA.

12. The method according to claim 4, wherein the transformation efficiency is higher than about $1\times10^8$ yeast transformants/µg vector DNA.

13. The method according to claim 5, wherein the transformation efficiency is higher than about $1\times10^8$ yeast transformants/µg vector DNA.

14. A method for producing an improved yeast library of proteins of interest in the form of a yeast surface display library comprising the steps of:
 a) providing a transfected yeast cells according to the method according to claim 3;
 b) diluting the transfected cells into a 1:1 mix of a solution of sorbitol in growth medium;
 c) resuspending cells in suitable growth medium;
 d) optionally, performing dilutions for a calculation of diversity, and plating said dilutions on SD-CAA plates containing kanamycin; and
 e) transferring said library into suitable growth medium and expanding said library per electroporation; and
 f) optionally, suitably storing said expanded library.

15. A method for producing an improved yeast library of proteins of interest in the form of a yeast surface display library comprising the steps of:
 a) providing a transfected yeast cells according to the method according to claim 4;
 b) diluting the transfected cells into a 1:1 mix of a solution of sorbitol in growth medium;
 c) resuspending cells in suitable growth medium;
 d) optionally, performing dilutions for a calculation of diversity, and plating said dilutions on SD-CAA plates containing kanamycin; and
 e) transferring said library into suitable growth medium and expanding said library per electroporation; and
 f) optionally, suitably storing said expanded library.

16. The method of claim 1, wherein the concentration of sorbitol is about 0.1 to about 10 M.

17. The method of claim 1, wherein the concentration of $CaCl_2$) is about 0.1 to about 10 mM.

18. The method of claim 1, wherein the concentration of lithium acetate is about 0.01 to about 1.0 M.

19. The method of claim 18, wherein the concentration of TCEP is about 1 to about 100 mM.

\* \* \* \* \*